(12) United States Patent
Ui et al.

(10) Patent No.: US 7,807,855 B2
(45) Date of Patent: Oct. 5, 2010

(54) PROCESS FOR PRODUCING HYDROXY COMPOUND

(75) Inventors: Toshiaki Ui, Niihama (JP); Tetsuya Suzuta, Niihama (JP); Tateo Seo, Chiba (JP)

(73) Assignee: Sumitomo Chemical Company, Limited, Tokyo (JP)

(*) Notice: Subject to any disclaimer, the term of this patent is extended or adjusted under 35 U.S.C. 154(b) by 359 days.

(21) Appl. No.: 11/576,479

(22) PCT Filed: Oct. 4, 2005

(86) PCT No.: PCT/JP2005/018720

§ 371 (c)(1),
(2), (4) Date: Apr. 2, 2007

(87) PCT Pub. No.: WO2006/038705

PCT Pub. Date: Apr. 13, 2006

(65) Prior Publication Data

US 2009/0048470 A1 Feb. 19, 2009

(30) Foreign Application Priority Data

Oct. 5, 2004 (JP) .............................. 2004-292339
Mar. 30, 2005 (JP) .............................. 2005-098187

(51) Int. Cl.
*C07C 37/02* (2006.01)
(52) U.S. Cl. .................................................... 568/796
(58) Field of Classification Search ................ 568/796; 345/10
See application file for complete search history.

(56) References Cited

U.S. PATENT DOCUMENTS

| 1,062,351 | A | * | 5/1913 | Meyer et al. ................. 568/739 |
| 1,963,761 | A | * | 6/1934 | Prahl .......................... 570/203 |
| 2,311,777 | A | * | 2/1943 | Redman ....................... 568/797 |
| 2,984,484 | A | * | 5/1961 | Congelli et al. .............. 473/100 |
| 2,988,573 | A | * | 6/1961 | Siebentritt et al. .......... 568/797 |
| 3,152,870 | A | * | 10/1964 | Duhaut et al. ................ 423/507 |
| 3,221,063 | A | | 11/1965 | Prahl et al. |
| 3,234,291 | A | * | 2/1966 | Kelly .......................... 568/796 |
| 3,303,223 | A | | 2/1967 | Kelly |
| 3,449,079 | A | * | 6/1969 | Van Dijk et al. ............. 423/506 |
| 3,449,679 | A | * | 6/1969 | Attwood ...................... 330/10 |
| 3,950,501 | A | * | 4/1976 | Chien et al. ................. 423/507 |
| 4,500,740 | A | * | 2/1985 | House ......................... 568/796 |
| 6,348,613 | B2 | * | 2/2002 | Miyamoto et al. ........... 558/274 |
| 6,962,682 | B2 | * | 11/2005 | Walsdorff et al. ........... 423/502 |
| 7,285,689 | B2 | * | 10/2007 | Stauffer ...................... 568/796 |
| 2001/0041806 | A1 | | 11/2001 | Miyamoto et al. |
| 2004/0052718 | A1 | * | 3/2004 | Walsdorff et al. ........... 423/502 |
| 2004/0179987 | A1 | | 9/2004 | Oku et al. |
| 2009/0048470 | A1 | | 2/2009 | Ui et al. |

FOREIGN PATENT DOCUMENTS

| EP | 1 099 666 A1 | 5/2001 |
| GB | 1 204 209 | 9/1970 |
| JP | 38-18369 B1 | 9/1963 |
| JP | 45-28366 | 9/1970 |
| JP | 50-34011 | 11/1975 |
| JP | 53-009723 | 1/1978 |
| JP | 2-72132 A | 3/1990 |
| JP | 2001-247518 A | 9/2001 |
| JP | 2003-81891 A | 3/2003 |

OTHER PUBLICATIONS

Louis Agnello, and William Williams, Ind. Eng. Chem., 1960, 52 (11), 894-900.*
E. C. Britton, Ind. Eng. Chem., 1941, 33 (8), 965-965.*
D. H. Killeffer, Ind. Eng. Chem., 1926, 18 (10), 1041-1046.*
Erwin Riedel: "Anorganische chemie", 1988, Walter De Gruyter, Berlin, New York, XP002552490, p. 373.

* cited by examiner

*Primary Examiner*—Brian J Davis
(74) *Attorney, Agent, or Firm*—Sughrue Mion, PLLC

(57) ABSTRACT

The invention provides a process for producing a hydroxy compound including the following steps:
(a) chlorination step: a step of producing a chlorinated hydrocarbon and hydrogen chloride from a hydrocarbon and chlorine;
(b) hydrolysis step: a step of producing a hydroxy compound and hydrogen chloride from the chlorinated hydrocarbon and water; and
(c) oxidation step: a step of producing chlorine by reaction of oxygen and hydrogen chloride obtained in the chlorination step and/or the hydrolysis step, and
(d) recycling at least a portion of the chlorine to the chlorination step.

7 Claims, 2 Drawing Sheets

PROCESS FOR PRODUCING HYDROXY COMPOUND

BACKGROUND OF THE INVENTION

1. Technical Field

The invention relates to a process for producing a hydroxy compound. More particularly, the Invention relates to a process for indirectly producing a hydroxy compound from a hydrocarbon, chlorine, and water via a chlorinated hydrocarbon, wherein the process is advantageous in that the hydrogen chloride gas produced as a by-product can be efficiently recycled and that the process is carried out without loss of the hydrocarbon by combustion or generation of dioxins.

2. Description of the Related Art

A process for indirectly producing a hydroxy compound such as phenol from a hydrocarbon, e.g. benzene, hydrogen chloride, and water via monochlorobenzene, a chlorinated hydrocarbon, is called as Raschig process and has been publicly known (for example, refer to U.S. Pat. No. 3,221,063). This is a process, in which monochlorobenzene is produced from benzene, hydrogen chloride and oxygen by oxychlorination method, then phenol is produced by hydrolyzing the monochlorobenzene and simultaneously hydrogen chloride produced as a by-product is recovered and used for oxychlorination method for the monochlorobenzene production.

However, in the oxychlorination method (refer to JP-A-53-9723), since hydrogen chloride, oxygen and benzene are kept co-existing at a high temperature of 200° C. or higher, benzene is apt to be lost by combustion and there is a risk of generation of dioxins. Further, processes involving oxychlorination methods to be carried out at a low temperature of 200° C. or lower are also disclosed (for example, refer to JP-B-45-28366 and 50-34011). However, the processes require use of costly noble metal catalysts, sometimes produce by-products such as diphenyl which are uneasy to be reused, also have a risk of generation of dioxins, and cannot cause a stable performance, and therefore it cannot be said that these processes are efficient production processes.

SUMMARY OF THE INVENTION

In view of the above state of the art, it is an object of the invention to provide a process for indirectly producing a hydroxy compound from a hydrocarbon, chlorine and water via a chlorinated hydrocarbon, in which the hydrogen chloride gas produced as a by-product can be efficiently recycled and which process is carried out without loss of the hydrocarbon by combustion or generation of dioxins.

That is, the invention provides a process for producing a hydroxy compound comprising the following steps:

chlorination step: a step of obtaining a chlorinated hydrocarbon and hydrogen chloride from a hydrocarbon and chlorine;

hydrolysis step: a step of obtaining a hydroxy compound and hydrogen chloride from the chlorinated hydrocarbon and water; and oxidation step: a step of obtaining chlorine by reaction of oxygen and hydrogen chloride obtained in the chlorination step and/or the hydrolysis step, and recycling at least a portion of the chlorine to the chlorination step.

Accordingly, the invention provides a process for indirectly producing a hydroxy compound from a hydrocarbon, chlorine and water via a chlorinated hydrocarbon, in which the hydrogen chloride gas produced as a by-product can be efficiently recycled and which process is carried out without loss of the hydrocarbon by combustion or generation of dioxins.

Figure 1:
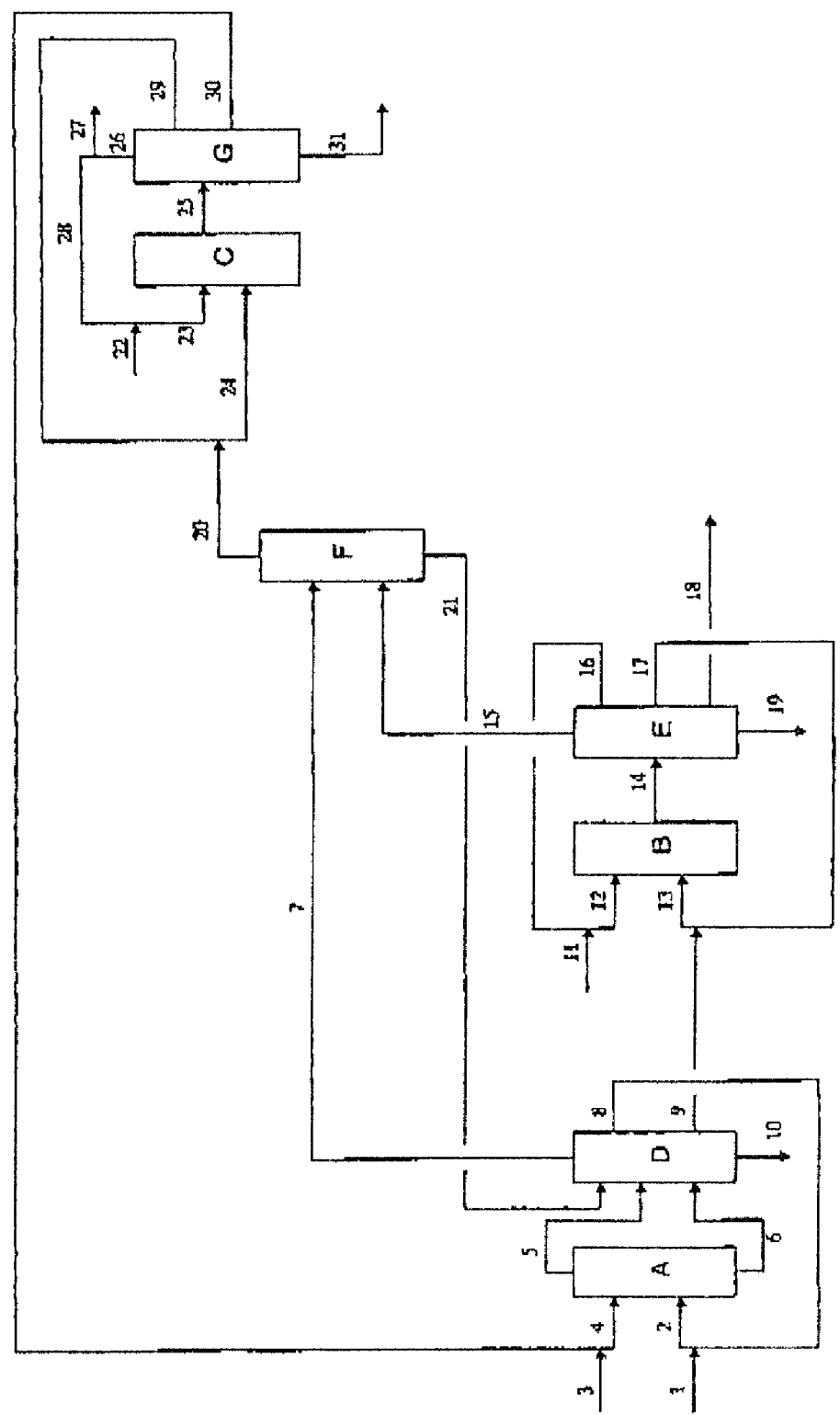
FIG. 1 shows an example of a flow for carrying out the invention, which is employed in Example 1.

A: Chlorination step
B: Hydrolysis step
C: Oxidation step
D: Chlorinated hydrocarbon refining step
E: Hydroxy compound refining step
F: Hydrogen chloride refining step
G: Chlorine separation and recovery step
L: Hydrolysis step
M: Hydrochloric acid separation step
N: Hydrogen chloride separation step
O: Hydroxy compound refining step

DETAILED DESCRIPTION OF THE INVENTION

The chlorination step of the invention is a step of obtaining a chlorinated hydrocarbon and hydrogen chloride by reaction of a hydrocarbon and chlorine.

The hydrocarbon used in the invention may be saturated or unsaturated hydrocarbons such as methane, ethane and propylene; aromatic hydrocarbons such as benzene, toluene and xylene; and those aromatic hydrocarbons of which the aromatic rings are substituted by substituent groups such as nitro groups, amino groups or alkyl groups. Further, the hydrocarbon may be polycyclic aromatic compounds such as naphthalene ring and anthracene ring other than the above-mentioned monocyclic aromatic compounds.

The chlorinated hydrocarbon obtained in the chlorination step of the invention may be chlorinated hydrocarbons such as methyl chloride, ethyl chloride and aryl chloride obtained by substituting one hydrogen atom of the linear hydrocarbons with one chlorine atom and such as carbon tetrachloride obtained by substituting hydrogen atoms of linear hydrocarbons with a plurality of chlorine atoms; and compounds such as monochlorobenzene, 1,2-, 1,3-, or 1,4-dichlorobenzene, 1,2,3-, 1,2,4-, or 1,3,5-trichlorobenzene, tetrachlorobenzene, pentachlorobenzene, hexachlorobenzene, mono- or polychlorotoluene, and mono- or polychloroxylene obtained by substituting hydrogen atoms of aromatic compounds with one or a plurality of chlorine atoms. Further, the chlorinated hydrocarbon may be those aromatic compounds of which an aromatic ring is substituted by substituent groups such as nitro group, amino group or alkyl groups. The chlorinated hydrocarbon may be polycyclic aromatic compounds such as naphthalene ring and anthracene ring other than the above-mentioned monocyclic aromatic compounds. Further, the chlorinated hydrocarbon may include not only those obtained by substituting directly an aromatic ring with chlorine atom but also compounds such as benzyl chloride and cumyl chloride obtained by chlorination of a substituent of an aromatic ring.

The chlorine used in the invention is not particularly limited and may be chlorine obtained by electrolysis of common salt, chlorine obtained by oxidizing hydrogen chloride and chlorine obtained by electrolysis of hydrochloric acid and/or hydrogen chloride.

Further, the above-mentioned kinds of chlorine may be used in a mixture at an optional mixing ratio.

The method for reacting the hydrocarbon and chlorine is not particularly limited and a conventionally known method may be employed. The method is practically exemplified as follows. The reaction may be carried out in liquid phase or vapor phase. The mole ratio of chlorine and the hydrocarbon (chlorine/hydrocarbon) may be 3 or lower: the reaction temperature may be 0 to 80° C.: and the reaction pressure may be a reduced pressure, a normal pressure or an increased pressure; however it Is generally a normal pressure. Depending on the hydrocarbon to be used, the reaction may be carried out without using any catalyst, however in the case of an aromatic hydrocarbon such as benzene, iron powder, ferric chloride, iodine, aluminum chloride, antimony pentachloride, Lewis acids such as various kinds of metal chlorides and solid acids such as zeolites and silica-alumina can be used as the catalyst.

The reaction mixture obtained in the chlorination step is generally subjected to gas-liquid separation and the gas is sent to the oxidation step as a mixture containing hydrogen chloride and the liquid is sent to the hydrolysis step as a portion containing the chlorinated hydrocarbon.

In the invention, it is preferable to employ the following chlorinated hydrocarbon refining step.

Chlorinated hydrocarbon refining step: a step of refining the chlorinated hydrocarbon obtained in the chlorination step.

The chlorinated hydrocarbon obtained in the chlorination step contains the hydrocarbon, which is a raw material for the chlorination step, and a small amount of by-product. A refined chlorinated hydrocarbon can be separated and recovered from the mixture. On the other hand, the hydrocarbon is separated and recovered in this step and at least a portion of the hydrocarbon may be recycled to the chlorination step.

To carry out the chlorinated hydrocarbon refining step, for example, distillation, extraction distillation, or adsorption separation may be employed. Particularly, in the case that the un-reacted hydrocarbon and the chlorinated hydrocarbon have different boiling points, distillation may be employed for the separation and in the case of separation of isomers of the chlorinated hydrocarbon having close boiling points, extraction distillation, adsorption separation or the like may be employed.

The hydrolysis step of the invention is a step of obtaining a hydroxy compound and hydrogen chloride from the chlorinated hydrocarbon and water.

The hydroxy compound to be obtained in the hydrolysis step of the invention may include alcohols, in which one hydroxy group bonds to a linear hydrocarbon, such as methanol, ethanol and allyl alcohol. alcohols, in which a plurality of hydroxy groups bond, such as pentaerythritol, and compounds, in which one or a plurality of hydroxy groups bond(s) to aromatic compounds, such as phenol, cresol, catechol, resorcin and hydroquinone. In the case of an aromatic compound, naphthol having naphthalene ring and a hydroxy compound having a polycyclic aromatic ring such as anthracene ring may be employed besides the above-mentioned monocyclic aromatic compounds. Further, not only the compounds in which hydroxyl group directly bonds to the aromatic ring but also compounds whose substituent group on an aromatic ring is hydroxylated such as benzyl alcohol and cumyl alcohol may be employed.

The method for reacting the chlorinated hydrocarbon and water is not particularly limited and a conventionally known method may be employed. The method is practically exemplified as follows. The reaction may be carried out in liquid phase or vapor phase. The mole ratio of water and the chlorinated hydrocarbon (water/chlorinated hydrocarbon) may be generally 0.5 or higher: the reaction temperature may be 600° C. or lower: and the reaction pressure may be a reduced pressure, a normal pressure or an increased pressure and it is generally a normal pressure.

As a catalyst may be used a supported phosphoric acid type catalyst, a supported copper type catalyst and the like, and a crystalline metallosilicate catalyst and/or a metal-bearing crystalline metallosilicate catalyst is preferable in terms of the activity and selectivity improvement of the hydrolysis reaction.

As the crystalline metallosilicate catalyst are preferably crystalline silicates containing Si as an indispensable component and one or more metal elements selected from Al, Cu, Ga, Fe, B, Zn, Cr, Be, Co, La, Ge, Ti, Zr, Hf, V, Ni, Sb, Bi, Nb and the like, and having 5 or higher atomic ratio of Si and other metals, that is, Si/Me atomic ratio (herein Me denotes one or more metal elements selected from Al, Cu, Ga, Fe, B, Zn, Cr, Be, Co, La, Ge, Ti, Zr, Hf, V, Ni, Sb, Bi, Nb and the like), however the catalyst may be a crystalline silicate containing silicon dioxide practically containing no Me component.

As the metal-bearing crystalline metallosilicate catalyst is employed those obtained by depositing the above-mentioned Me components on such a crystalline metallosilicate.

Raw materials to be supplied to the hydrolysis process are the chlorinated hydrocarbon and water and in the invention, hydrochloric acid consisting of the hydrogen chloride recovered in the hydrolysis step and unreacted water (that is, an aqueous hydrogen chloride solution) may be used in place of the water as a raw material. In this case, water in the hydrochloric acid contributes to the reaction and is lost, however as hydrogen chloride is produced as a by-product, the hydrogen chloride concentration in the hydrochloric acid recovered in the hydrolysis step increases by carrying out the hydrolysis reaction.

In the case of reacting the chlorinated hydrocarbon and hydrochloric acid, the method for the reaction is not particularly limited and it may be carried out by replacing water with hydrochloric acid in the method of using water.

The hydrochloric acid to be used is not particularly limited and may be hydrochloric acid produced in other steps or processes.

The hydrogen chloride concentration in the hydrochloric acid is desirable to be so as to cause no adverse effect of the hydrogen chloride on the hydrolysis reaction. It is supposed that the hydrogen chloride concentration in the hydrochloric acid may differ in accordance with the type of the chlorinated hydrocarbon to be used, the conditions of the hydrolysis reaction, and the catalyst for the hydrolysis reaction, however it is preferable to be 21% by weight or lower in the case when monochlorobenzene is hydrolyzed using a crystalline metallosilicate catalyst and/or a metal-bearing crystalline metallosilicate catalyst.

In the invention, it is preferable to employ the following hydroxy compound refining step.

Hydroxy compound refining step: a step of refining the hydroxy compound obtained in the hydrolysis step.

The hydroxy compound obtained in the hydrolysis step contains the chlorinated hydrocarbon, which is a raw material in the hydrolysis step, and a small amount of by-product. A refined hydroxy compound can be separated and recovered from the mixture. On the other hand, the chlorinated hydrocarbon is separated and recovered in this step and at least a portion of it may be recycled to the hydrolysis step. To carry out the hydroxy compound refining step, for example distillation, extraction distillation or the like may be employed.

In the invention, it is preferable to employ the following hydrochloric acid separation step and hydrogen chloride separation step.

Hydrochloric acid separation step: a step of separating the mixture obtained in the hydrolysis step into a portion containing mainly hydrochloric acid and a portion containing mainly the hydrocarbon, the chlorinated hydrocarbon and the hydroxy compound.

Hydrogen chloride separation step: a step of separating a portion containing mainly hydrogen chloride from the portion containing mainly hydrochloric acid obtained in the hydrochloric acid separation step and sending the separated portion to the oxidation step and recycling the remainder to the hydrolysis step.

In the hydrochloric acid separation step, since the mixture obtained in the hydrolysis step breaks up into an oil layer containing mainly organic materials such as the hydrocarbon, the chlorinated hydrocarbon and the hydroxy compound and a hydrochloric acid layer containing mainly unreacted water and the produced hydrogen chloride, the hydrochloric acid layer can be separated by a conventionally known oil-water separation operation. In the case separation of the oil layer and the hydrochloric acid layer is insufficient the oil layer and the hydrochloric acid layer may be separated by extraction operation using an organic solvent with low mutual solubility with hydrochloric acid. Further, it is also preferable to remove very small amounts of the organic materials such as the hydroxy compound, the chlorinated hydrocarbon, the hydrocarbon and the organic solvent contained in the recovered hydrochloric acid layer by extraction operation or the like.

Just after starting operation of the hydrolysis step or in the case water used in the hydrolysis step is in a very large amount, the concentration of hydrogen chloride in the portion containing mainly hydrochloric acid obtained in the hydrochloric acid separation step sometimes becomes lower than the azeotropic composition of hydrogen chloride and water under the operation pressure in the next hydrogen chloride separation step. In such a case that the concentration of hydrogen chloride in the portion containing mainly hydrochloric acid obtained in the hydrochloric acid separation step is low, it is preferable that the next hydrogen chloride separation step is not carried out and the portion containing mainly hydrochloric acid is directly sent to the hydrolysis step and used as water in the hydrolysis step. To do so, the concentration of hydrogen chloride is gradually increased.

The hydrogen chloride separation step is normally a step of separating hydrogen chloride by distillation. As described above, when the concentration of hydrogen chloride in the portion containing mainly hydrochloric acid is sufficiently high, the step is preferably carried out. When hydrochloric acid (more preferably hydrochloric acid in an azeotropic composition of hydrogen chloride and water under the operation pressure in the hydrogen chloride separation step) is used as water in the hydrolysis step, it is preferable that the hydrogen chloride corresponding to the concentration increase of the hydrolysis step is recovered in the hydrogen chloride separation step and the remaining hydrochloric acid is used as a raw material for the hydrolysis step. The hydrogen chloride separation step is generally carried out by using a distillation tower; and in the case the concentration of hydrogen chloride is sufficiently high, hydrogen chloride is recovered by distillation at the summit of the tower and the remaining hydrochloric acid is obtained in the bottom of the tower and the operation pressure of the distillation tower is preferably 0.1 to 1.0 MPa and more preferably 0.1 to 0.7 MPa. The concentration of the remaining hydrochloric acid at that time is just to give an azeotropic composition in accordance with the operation pressure and becomes 21% by weight at 0.1 MPa and 13% by weight at 1.0 MPa. If the operation pressure is too low, the step requires a vacuum facility, thereby resulting in an increase of installation cost and an increase of the remaining hydrochloric acid concentration and therefore a decrease of hydrogen chloride recovery ratio. On the other hand, if the operation pressure is too high, the remaining hydrochloric acid concentration is lowered and the hydrogen chloride recovery ratio is increased; however, corrosion of the apparatus materials tends to progress since the tower bottom temperature is increased and also the step requires a high temperature heating source and therefore, it is not preferable in terms of saving energy.

The hydrogen chloride separated by distillation is sent to the oxidation step, however it may be also usable for various kinds of uses using hydrogen chloride and practically, it may be used as a raw material for oxychlorination.

In the invention, it is preferable to employ the following hydrogen chloride refining step.

Hydrogen chloride refining step: a step of refining hydrogen chloride from the mixture containing hydrogen chloride obtained in the chlorination step and/or the hydrogen chloride separation step and sending it to the oxidation step.

The refining method in this step may be a method of obtaining refined hydrogen chloride in the form of a gas by gas-liquid separation by cooling the mixture and a method of removing impurities by adsorption, and these methods are preferably employed in combination.

In the case the hydrogen chloride refining step is carried out for the mixture containing hydrogen chloride obtained in the chlorination step and the hydrogen chloride separation step, the mixture containing hydrogen chloride obtained in the chlorination step and the mixture containing hydrogen chloride obtained in the hydrogen chloride separation step may be treated together or may be treated separately by employing the hydrogen chloride refining step that treats the mixture containing hydrogen chloride obtained in the chlorination step after the chlorination step and employing the hydrogen chloride refining step that treats the mixture containing hydrogen chloride obtained in the hydrogen chloride separation step after the hydrogen chloride separation step, respectively.

The oxidation step of the invention is a step of obtaining chlorine by reaction of oxygen and hydrogen chloride obtained in the chlorination step and/or the hydrolysis step, and recycling at least a portion of the chlorine to the chlorination step. As described above, the hydrogen chloride may be a portion containing mainly hydrogen chloride obtained in the above-mentioned hydrogen chloride refining step.

The method for reacting the hydrogen chloride and oxygen is not particularly limited and a conventionally known method may be employed. The method is practically exemplified as follows. The mole ratio of hydrogen chloride and oxygen (hydrogen chloride/oxygen) may be 0.5 to 2: the reaction temperature may be 200 to 500° C. and preferably 200 to 380° C.: the reaction pressure may be 0.1 to 5 MPa: and the superficial velocity may be 0.7 to 10 m/s. As a reactor may be employed a fixed bed reactor, a fluidized bed reactor and a moving-bed reactor. As a catalyst may be used a chromium oxide catalyst and a ruthenium oxide catalyst for the reaction.

In the invention, it is preferable to employ the following chlorine separation and recovery step.

Chlorine separation and recovery step: a step of separating the reaction mixture of the oxidation step into a portion containing mainly chlorine, a portion containing mainly hydrogen chloride, a portion containing mainly oxygen and a portion containing mainly water, recycling at least a part of the portion containing mainly chlorine to the chlorination step, and recycling at least a part of the portion containing mainly hydrogen chloride and at least a part of the portion containing mainly oxygen to the oxidation step.

The reaction mixture of the oxidation step contains chlorine, hydrogen chloride, water and oxygen. These respective components each are separated in this step and chlorine, hydrogen chloride and oxygen are recovered.

To carry out the chlorine separation and recovery step, for example, absorption, condensation and distillation may be employed. With respect to hydrogen chloride and water, after being condensed or absorbed in a solvent, hydrogen chloride can be recovered by stripping or distillation and recycled to the oxidation step. Additionally, the solvent to absorb hydrogen chloride and water may be water or an aqueous hydrochloric acid solution. Chlorine and oxygen can be separated by distillation Separated oxygen may be recycled to the oxidation step. Separated chlorine may be recycled to the chlorination step.

In the process for producing a hydroxy compound of the invention, a method of obtaining monochlorobenzene as the chlorinated hydrocarbon by using benzene as the hydrocarbon and successively obtaining phenol as the hydroxy compound is particularly important from a viewpoint of industry and the invention is preferably applicable thereto.

EXAMPLES

Next, the invention will be described with reference to Examples.

Example 1

In the case of using benzene as a hydrocarbon and obtaining phenol as a hydroxy compound, the invention can be carried out according to the flow shown in FIG. 1 and material balance shown in Table 1.

Benzene (fluid No. 2) and chlorine (fluid No. 4) are supplied to a chlorination step (A) and chlorination reaction is carried out using a catalyst to produce monochlorobenzene and hydrogen chloride and obtain a reaction solution (fluid No. 6) containing monochlorobenzene and unreacted benzene and a gas (fluid No. 5) containing mainly hydrogen chloride. The obtained reaction solution and the gas containing mainly hydrogen chloride are supplied to a chlorinated hydrocarbon refining step (D) and separated by distillation to a crude hydrogen chloride gas (fluid No. 7) including benzene and monochlorobenzene, a fraction (fluid No. 8) containing mainly benzene, a fraction (fluid No. 9) containing mainly monochlorobenzene and a fraction (fluid No. 10) containing mainly impurities. Together with new benzene (fluid No. 1), the fraction containing mainly benzene is supplied to the chlorination step and used as a reaction raw material. The fraction containing mainly monochlorobenzene is supplied to a hydrolysis step (B).

Next, after monochlorobenzene (fluid No. 13) and water (fluid No. 12) are supplied to the hydrolysis step and heated and evaporated, hydrolysis reaction is carried out using a catalyst to produce phenol and hydrogen chloride. The reaction gas (fluid No. 14) containing produced phenol, hydrogen chloride, unreacted monochlorobenzene and water is supplied to a hydroxy compound refining step (E) and separated by distillation to a crude hydrogen chloride gas (fluid No. 15) including monochlorobenzene, a fraction (fluid No. 16) containing mainly water, a fraction (fluid No. 17) containing mainly monochlorobenzene, a fraction (fluid No. 18) containing mainly phenol and a fraction (fluid No. 19) containing mainly impurities. The fraction containing mainly monochlorobenzene is supplied to the hydrolysis step together with the fraction (fluid No. 9) containing mainly monochlorobenzene obtained in the chlorinated hydrocarbon refining step and utilized as a reaction raw material.

The crude hydrogen chloride gases obtained in the chlorinated hydrocarbon refining step and the hydroxy compound refining step are supplied to a hydrogen chloride refining step (F), and benzene and monochlorobenzene in the gases are liquefied and adsorbed for separation to obtain refined hydrogen chloride gas (fluid No. 20) and a benzene/monochlorobenzene mixture (fluid No. 21). The obtained benzene/monochlorobenzene mixture is supplied to the chlorinated hydrocarbon refining step.

Next, the refined hydrogen chloride gas obtained in the hydrogen chloride refining step and oxygen (fluid No. 23) are supplied to an oxidation step (C) to produce chlorine and water by oxidation reaction using a catalyst. The reaction gas (fluid No. 25) containing produced chlorine and water as well as unreacted hydrogen chloride and oxygen is supplied to a chlorine separation and recovery step (G) and separated by condensation liquefaction and distillation to a gas (fluid No 26) containing mainly oxygen, a gas (fluid No. 29) containing mainly hydrogen chloride, a gas (fluid No. 30) containing mainly chlorine and a fraction (fluid No. 31) containing mainly water. A portion (fluid No. 27) of the gas containing mainly oxygen is purged for preventing impurity accumulation and together with new oxygen (fluid No. 22), the remaining (fluid No. 28) is supplied to the oxidation step and utilized as a reaction raw material. Together with the refined hydrogen chloride gas obtained in the hydrogen chloride refining step, the gas containing mainly hydrogen chloride is supplied to the oxidation step and utilized as a reaction raw material. Together with new chlorine (fluid No. 3) the gas containing mainly chlorine is supplied to the chlorination step and utilized as a reaction raw material.

TABLE 1

| | 1 | 2 | 3 | 4 | 5 | 6 | 7 | 8 | 9 | 10 | 11 |
|---|---|---|---|---|---|---|---|---|---|---|---|
| | | | | | Mass flow rate [kg/h] | | | | | | |
| Benzene | 847.9 | 5707.0 | | | 78.6 | 4772.5 | 48.6 | 4859.1 | | | |
| Chlorine | | | 2.8 | 778.1 | | | | | | | |
| Monochlorobenzene | | | | | 11.2 | 1220.3 | 1.2 | | 1233.9 | 5.0 | |
| Hydrogen chloride | | | | | 380.1 | 20.0 | 400.1 | | | | |
| Water | | | | | | | | | | | 203.2 |
| Phenol | | | | | | | | | | | |
| Oxygen | | | | | | | | | | | |
| Impurities | | | | | | | 2.4 | | | | 2.4 |
| Total | 847.9 | 5707.0 | 2.8 | 778.1 | 469.9 | 6015.2 | 449.9 | 4859.1 | 1233.9 | 7.4 | 203.2 |

TABLE 1-continued

| | 12 | 13 | 14 | 15 | 16 | 17 | 18 | 19 | 20 | 21 | 22 |
|---|---|---|---|---|---|---|---|---|---|---|---|
| | | | | | Mass flow rate [kg/h] | | | | | | |
| Benzene | | 4.0 | 12.0 | 8.0 | | 4.0 | | | | 56.6 | |
| Chlorine | | | | | | | | | | | |
| Monocholorobenzene | | 4906.1 | 3679.6 | 7.4 | | 3672.2 | | | | 8.6 | |
| Hydrogen chloride | | | 397.3 | 397.3 | | | | | 797.4 | | |
| Water | 1972.0 | | 1768.8 | | 1768.8 | | | | | | |
| Phenol | | | 1005.0 | | | | | 1000.0 | 5.0 | | |
| Oxygen | | | | | | | | | | | 182.1 |
| Impurities | | | 6.5 | | | | | | 6.5 | | 0.5 |
| Total | 1972.0 | 4910.1 | 6869.2 | 412.7 | 1768.8 | 3676.2 | 1000.0 | 11.5 | 797.4 | 65.2 | 182.5 |

| | 23 | 24 | 25 | 26 | 27 | 28 | 29 | 30 | 31 |
|---|---|---|---|---|---|---|---|---|---|
| | | | | Mass flow rate [kg/h] | | | | | |
| Benzene | | | | | | | | | |
| Chlorine | 2.3 | | 777.6 | 2.3 | 2.3 | 0.1 | | 775.3 | |
| Monochlorobenzene | | | | | | | | | |
| Hydrogen chloride | | 938.1 | 140.7 | | | | 140.7 | | |
| Water | | | 197.0 | | | | | | 197.0 |
| Phenol | | | | | | | | | |
| Oxygen | 411.7 | | 236.7 | 236.7 | 229.6 | 7.1 | | | |
| Impurities | 15.4 | | 15.4 | 15.4 | 14.9 | 0.5 | | | |
| Total | 429.3 | 938.1 | 1367.5 | 254.4 | 246.8 | 7.6 | 140.7 | 775.3 | 197.0 |

Reference Example 1

Reaction Example of Hydrolysis Step

The conversion to monochlorobenzene and the selectivity to phenol in Reference Example 1 are defined as follows.
Conversion to monochlorobenzene (%)=(mole amount of reacted monochlorobenzene)/(mole amount of supplied monochlorobenzene)×100
Selectivity to phenol (%)=(mole amount of produced phenol)/(mole amount of reacted monochlorobenzene)×100
Selectivity to benzene (%)=(mole amount of produced benzene)/(mole amount of reacted monochlorobenzene)×100

An aqueous copper chloride solution was produced by stirring and dissolving 10.0 g of commercialized copper chloride dehydrate (manufactured by Wako Pure Chemical Industries, Ltd.: 99.9% by weight PUA) in 40 ml of ion exchange water. The aqueous copper chloride solution was mixed with 20.0 g of commercialized H-ZSM-5 zeolite (manufactured by N. E. CHEMCAT CORPORATION: Si/Al=15: an extrusion molded product with 1.6 mmϕ) and stirred by a stirrer for 8 hours to carry out ion exchange. The solid matter was separated by filtration and washed with ion exchange water and successively dried at 120° C. for 4 hours and fired at 400° C. for 5 hours in air current to obtain a catalyst. The Cu content of the obtained catalyst was measured by an alkali fusion/ICP-AES method to find that it was 3.0% by weight.

A fixed bed reactor made of quartz and having an inner diameter of 17 mmϕ was filled with 1 g of the catalyst and kept at 454° C. The fixed bed evaporator was filled with SiC and kept at 200° C. while nitrogen was circulated at 11 ml/min speed and an aqueous 17% hydrochloric acid solution was supplied at 0.65 g/h speed and also monochlorobenzene (manufactured by Wako Pure Chemical Industries, Ltd.: first grade) was supplied at 3.16 g/h to the fixed bed evaporator to start reaction.

After 1.5 hours, the produced gas was absorbed in toluene and the produced material was analyzed by gas chromatography to find that the conversion to monochlorobenzene was 11.8%, selectivity to phenol was 92.5%, and selectivity to benzene was 5.6%.

Example 2

Figure 2:
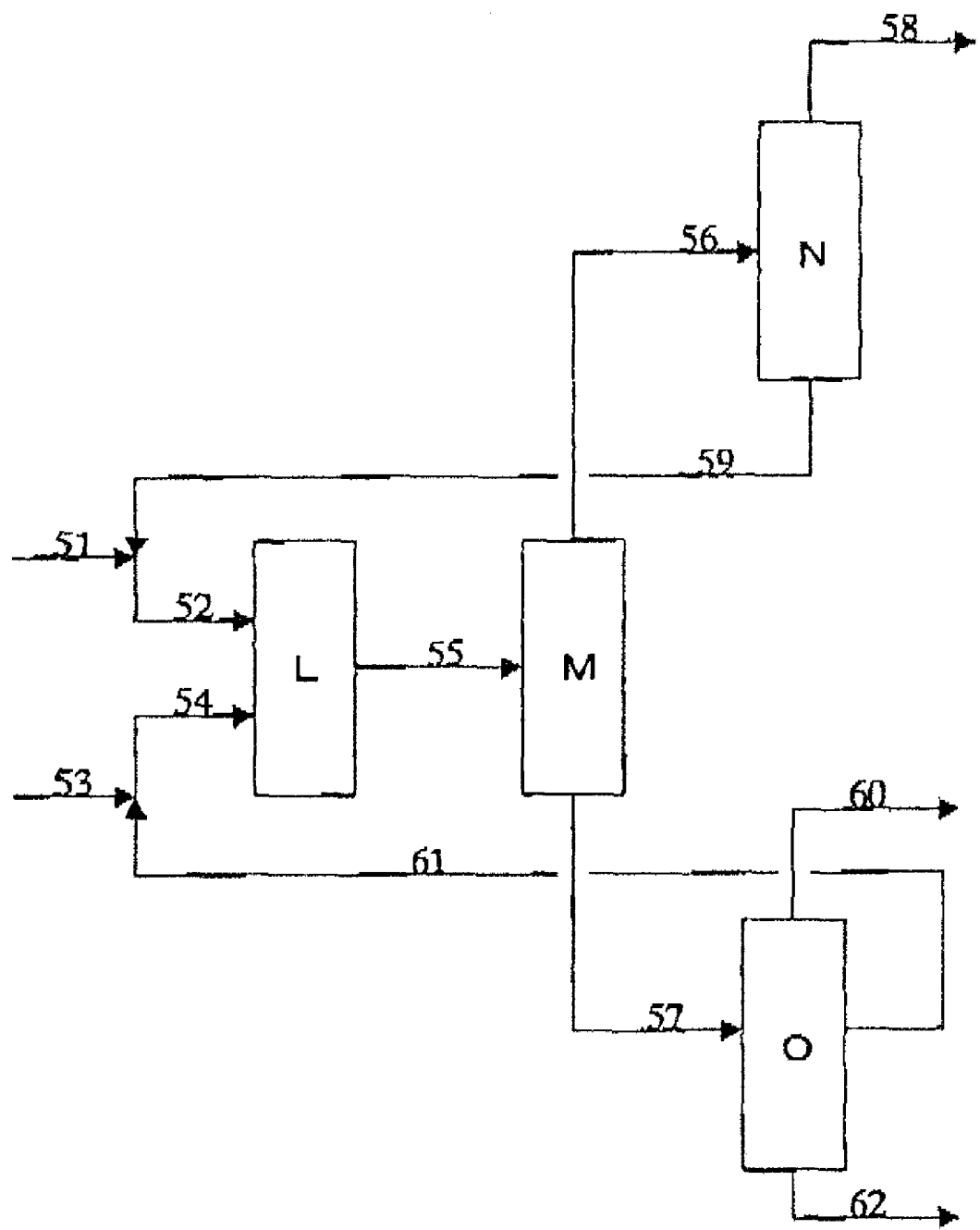
FIG. 2 shows an example of a flow for carrying out the invention, which is employed in Example 2.

In the invention, in the case that using hydrochloric acid as water that Is one of raw materials for the hydrolysis step, the hydrolysis step, the hydrochloric acid separation step, the hydrogen chloride separation step and the hydroxy compound refining step are carried out, the invention can be carried out most properly according to, for example, the flow shown in FIG. 2 and material balance shown in Table 2.

After monochlorobenzene (fluid No. 54) and hydrochloric acid (fluid No. 52: hydrogen chloride concentration 19.4% by weight) are supplied to the hydrolysis step (L) and heated and evaporated, reaction of monochlorobenzene and water is carried out in a reactor filled with a copper-bearing zeolite catalyst to produce phenol and hydrogen chloride. In this case, benzene is produced by a side reaction.

The reaction mixture (fluid No. 55) containing the produced phenol, hydrogen chloride and benzene as well as unreacted monochlorobenzene and water is supplied to a hydrochloric acid separation step (M) and separated to a hydrochloric acid layer (fluid No. 56) containing mainly hydrogen chloride and water and an oil layer (fluid No. 57) containing mainly phenol, monochlorobenzene and benzene.

The hydrochloric acid layer obtained in the hydrochloric acid separation step was supplied to a hydrogen chloride separation step (N) and hydrogen chloride gas was released in a distillation tower to obtain a gas (fluid No. 58) containing mainly hydrogen chloride from the summit part and from the tower bottom hydrochloric acid (fluid No. 59) with a decreased hydrogen chloride concentration lower than that of the supplied raw material of the distillation tower. The hydrochloric acid obtained from the tower bottom is supplied to the hydrolysis step together with water (fluid No. 51) supplied from the outside and utilized as a reaction raw material.

The oil layer obtained in the hydrochloric acid separation step is supplied to the hydroxy compound refining step and separated by distillation to a fraction (fluid No. 60) containing mainly benzene, a fraction (fluid No. 61) containing mainly monochlorobenzene and a fraction (fluid No. 62) containing mainly phenol. Together with new monochlorobenzene (fluid No. 53) supplied from the outside, the fraction containing mainly monochlorobenzene is supplied to the hydrolysis step and utilized as a reaction raw material. The fraction containing mainly benzene can be utilized as a production raw material of monochlorobenzene.

TABLE 2

| Fluid No. | 51 | 52 | 53 | 54 | 55 | 56 | 57 | 58 | 59 | 60 | 61 | 62 |
|---|---|---|---|---|---|---|---|---|---|---|---|---|
| Flow rate by mole [kmol/h] | | | | | | | | | | | | |
| Monochlorobenzene | | | 10.6 | 89.9 | 79.2 | 0.0 | 79.2 | | | | 79.2 | |
| Water | 10.5 | 112.3 | | | 101.8 | 101.8 | | | 101.8 | | | |
| Phenol | | | | | 10.0 | | 10.0 | | | | | 10.0 |
| Hydrogen chloride | | 13.4 | | | 24.0 | 24.0 | | 10.6 | 13.4 | | | |
| Benzene | | | | | 0.6 | | | | | 0.6 | | |
| Total | 10.5 | 125.7 | 10.6 | 89.9 | 215.7 | 125.9 | 89.2 | 10.6 | 115.2 | 0.6 | 79.2 | 10.0 |
| Mass flow rate [kg/h] | | | | | | | | | | | | |
| Monocholorobenzene | | | 1199 | 10116 | 8918 | | 8918 | | | | 8918 | |
| Water | 190 | 2024 | | | 1834 | 1834 | | | 1834 | | | |
| Phenol | | | | | 941 | | 941 | | | | | 941 |
| Hydrogen chloride | | 488 | | | 876 | 876 | | 388 | 488 | | | |
| Benzene | | | | | 47 | | 47 | | | 47 | | |
| Total | 190 | 2512 | 1199 | 10116 | 12617 | 2710 | 9906 | 388 | 2322 | 47 | 8918 | 941 |

INDUSTRIAL APPLICABILITY

As described above in detail, the invention provides a process for indirectly producing a hydroxy compound from a hydrocarbon, chlorine and water via a chlorinated hydrocarbon, in which the hydrogen chloride gas produced as a by-product can be efficiently recycled and which process is carried out without loss of the hydrocarbon by combustion or generation of dioxins. Further, the invention also provides a method for efficiently utilizing hydrochloric acid (an aqueous hydrogen chloride solution) produced as a by-product from hydrogen chloride produced in the hydrolysis step in the process and unreacted water and accordingly, the invention has a considerably significant industrial value for application.

What is claimed is:

1. A process for producing a hydroxy compound comprising the following steps:
   (a) chlorination step: a step of producing a chlorinated hydrocarbon and hydrogen chloride from a hydrocarbon and chlorine, wherein the chlorine is supplied to the chlorination step;
   (b) hydrolysis step: a step of producing a hydroxy compound and hydrogen chloride from the chlorinated hydrocarbon supplied from the chlorination step and water, wherein the water is supplied to the hydrolysis step; and
   (c) oxidation step: a step of producing chlorine by reaction of oxygen and hydrogen chloride obtained in the chlorination step and/or the hydrolysis step, and
   (d) recycling at least a portion of the chlorine produced in the oxidation step (c) to the chlorination step,
   wherein the hydrocarbon is an aromatic compound, the chlorinated hydrocarbon is a chlorinated aromatic compound, and the hydroxyl compound is an aromatic hydroxyl compound.

2. The process according to claim 1 further comprising the following hydrochloric acid separation step (e) and hydrogen chloride separation step (f):
   (e) hydrochloric acid separation step: a step of separating the mixture obtained in the hydrolysis step into a portion containing hydrochloric acid and a portion containing the hydrocarbon, the chlorinated hydrocarbon and the hydroxy compound; and
   (f) hydrogen chloride separation step: a step of separating a portion containing hydrogen chloride from the portion containing hydrochloric acid obtained in the hydrochloric acid separation step and sending the separated portion containing hydrogen chloride to the oxidation step and recycling the remainder to the hydrolysis step.

3. The process according to claim 1 or 2 further comprising the following hydrogen chloride refining step (g):
   (g) hydrogen chloride refining step: a step of refining hydrogen chloride from the mixture containing hydrogen chloride obtained in the chlorination step and/or the hydrogen chloride separation step by gas-liquid separation by cooling the mixture and by removing impurities by adsorption to produce refined hydrogen chloride in the form of a gas and sending the resulting hydrogen chloride gas to the oxidation step.

4. The process according to claim 1 further comprising the following chlorine separation and recovery step (h) and step (i):
   (h) chlorine separation and recovery step: a step of separating the resulting reaction mixture of the oxidation step into a portion containing chlorine, a portion containing hydrogen chloride, a portion containing oxygen and a portion containing water, recycling at least a part of the portion containing chlorine to the chlorination step, and
   (i) recycling at least a part of the portion containing hydrogen chloride and at least a part of the portion containing oxygen to the oxidation step.

5. The process according to claim 1 further comprising the following chlorinated hydrocarbon refining step (j):
   (j) chlorinated hydrocarbon refining step: a step of refining the chlorinated hydrocarbon obtained in the chlorination step by distillation, extraction distillation, or adsorption separation.

6. The process according to claim 1 further comprising the following hydroxy compound refining step (k):
 (k) hydroxy compound refining step: a step of refining the hydroxy compound obtained in the hydrolysis step by distillation, or extraction distillation.

7. The process according to claim 1, wherein the hydrocarbon is benzene, the chlorinated hydrocarbon is monochlorobenzene, and the hydroxy compound is phenol.

* * * * *